(12) United States Patent
Jezierski et al.

(10) Patent No.: US 11,035,631 B2
(45) Date of Patent: Jun. 15, 2021

(54) COUNTERMASS LIQUID FOR A SHOULDER LAUNCHED MUNITION PROPULSION SYSTEM

(71) Applicant: Nammo Defense Systems Inc., Mesa, AZ (US)

(72) Inventors: Dominic Jezierski, Chandler, AZ (US); Jerry Lambert, Dixon, CA (US); Harry Blomquist, Gilbert, AZ (US); Stephen Joseph Early, Mesa, AZ (US); Bill Goodwin, Gilbert, AZ (US)

(73) Assignee: Nammo Defense Systems Inc., Mesa, AZ (US)

( * ) Notice: Subject to any disclaimer, the term of this patent is extended or adjusted under 35 U.S.C. 154(b) by 0 days.

(21) Appl. No.: 15/507,476

(22) PCT Filed: Feb. 27, 2017

(86) PCT No.: PCT/US2017/019749
§ 371 (c)(1),
(2) Date: Feb. 28, 2017

(87) PCT Pub. No.: WO2017/172170
PCT Pub. Date: Oct. 5, 2017

(65) Prior Publication Data
US 2018/0347923 A1 Dec. 6, 2018

Related U.S. Application Data

(60) Provisional application No. 62/301,269, filed on Feb. 29, 2016.

(51) Int. Cl.
*C07C 51/02* (2006.01)
*F41A 1/10* (2006.01)

(52) U.S. Cl.
CPC .............. *F41A 1/10* (2013.01); *C07C 51/02* (2013.01)

(58) Field of Classification Search
None
See application file for complete search history.

(56) References Cited

U.S. PATENT DOCUMENTS

| 1,108,714 | A | 8/1914 | Davis |
| 1,108,715 | A | 8/1914 | Davis |
| (Continued) | | | |

FOREIGN PATENT DOCUMENTS

| GB | 2183800 A | 6/1987 |
| WO | 2017172170 A3 | 12/2017 |

OTHER PUBLICATIONS

Supplementary European Search Report for EU Application No. EP17803190 Supplementary Search Report dated Aug. 2, 2019.
(Continued)

*Primary Examiner* — Joseph D Anthony
(74) *Attorney, Agent, or Firm* — Devlin Law Firm LLC; Paul M. Richter, Jr.

(57) ABSTRACT

A countermass liquid for a shoulder launched propulsion system that has low corrosivity, high density, low viscosity, and a constant viscosity as a function of temperature. Upon function of the shoulder launched propulsion system, the countermass liquid may be expelled through the breach end of the shoulder launched propulsion system by expanding propellant gas. The countermass liquid may be an organic salt selected from the group consisting of at least one or more of cesium formate and potassium formate.

15 Claims, 5 Drawing Sheets

(56) References Cited

U.S. PATENT DOCUMENTS

| | | | |
|---|---|---|---|
| 1,108,717 A | | 8/1914 | Davis |
| 1,395,630 A | | 11/1921 | Davis |
| 2,156,605 A | | 5/1939 | prettyman |
| 3,149,531 A | | 9/1964 | Musgrave |
| 3,279,319 A | | 10/1966 | Semonian |
| 3,307,451 A | | 3/1967 | Ludwig |
| 3,800,656 A | | 4/1974 | Schnabele |
| 4,132,148 A | | 1/1979 | Meistring et al. |
| 4,244,293 A | | 1/1981 | Grosswendt et al. |
| 4,484,524 A | | 11/1984 | Dawant et al. |
| 4,554,860 A | | 11/1985 | Johansson et al. |
| 5,337,648 A | | 8/1994 | Brage |
| 5,551,330 A | | 9/1996 | Reuche |
| 5,874,474 A | * | 2/1999 | Peterson ............... A61K 31/19 514/557 |
| 5,952,601 A | | 9/1999 | Sanford et al. |
| 6,214,889 B1 | * | 4/2001 | Peterson ............... A61K 31/19 514/557 |
| 6,543,329 B2 | | 4/2003 | Sanford et al. |
| 6,971,299 B2 | | 12/2005 | Franzen et al. |
| 7,353,739 B2 | | 4/2008 | Ax et al. |
| 7,624,668 B1 | | 12/2009 | Sanford |
| 7,814,696 B2 | | 10/2010 | Rapp et al. |
| 7,823,497 B2 | | 11/2010 | Ostberg et al. |
| 8,220,376 B2 | | 7/2012 | Jonsson |
| 8,448,556 B2 | | 5/2013 | Regebro |
| 8,707,847 B2 | | 4/2014 | Wang et al. |
| 2002/0112601 A1 | | 8/2002 | Sanford et al. |
| 2004/0035580 A1 | * | 2/2004 | Bouwmeester ...... C09K 8/5045 166/295 |
| 2005/0101491 A1 | * | 5/2005 | Vollmer ............... C08L 1/284 507/112 |
| 2005/0107264 A1 | * | 5/2005 | van Batenburg ........ C09K 8/08 507/211 |
| 2006/0009649 A1 | * | 1/2006 | Murray ............... C07C 51/487 554/194 |
| 2006/0169175 A1 | * | 8/2006 | Lende ............... C04B 28/02 106/638 |
| 2007/0068374 A1 | | 3/2007 | Ostberg et al. |
| 2007/0261848 A1 | * | 11/2007 | Benton ............... C09K 8/506 166/288 |
| 2010/0204511 A1 | * | 8/2010 | Horton ............... E21B 21/068 562/512 |
| 2012/0055237 A1 | * | 3/2012 | Sweeney ............... F17D 1/05 73/49.5 |
| 2012/0204750 A1 | | 8/2012 | Sullivan et al. |
| 2014/0007758 A1 | | 1/2014 | Wang et al. |
| 2014/0262283 A1 | * | 9/2014 | Savari ............... E21B 21/003 166/305.1 |
| 2014/0265074 A1 | * | 9/2014 | Goossens ............... F16F 13/08 267/140.13 |
| 2014/0343413 A1 | | 11/2014 | Jolck et al. |
| 2015/0144565 A1 | * | 5/2015 | Kaminski ............ B01D 17/0202 210/664 |
| 2015/0152033 A1 | * | 6/2015 | Bakke ............... C07C 51/02 562/609 |
| 2016/0376488 A1 | * | 12/2016 | Galindo ............... C09K 8/12 175/65 |

OTHER PUBLICATIONS

Notice of Allowance dated Jul. 22, 2019, U.S. Appl. No. 15/507,495.
Formate Technical Manual. Technical Manual (online), Cabot Corporation, (2013) Retrieved on May 7, 2019. Retrieved from the internet: http://www.cabotcorp.com/solutions/porducts-plus/cesium-formate-brines/formate-technical-manual.
International Search Report for International Application No. PCT/US2017/019749, International Search Report dated Nov. 3, 2017.
International Search Report for International Application No. PCT/US2017/019764, International Search Report dated Dec. 26, 2017.
Nonfinal Office Action dated Oct. 15, 2018, U.S. Appl. No. 15/507,495.
Notice of Allowance dated Apr. 16, 2019, U.S. Appl. No. 15/507,495.
Supplementary European Search Report for EU Application No. EP17776176 Supplementary Search Report dated Jul. 23, 2019.

* cited by examiner

COUNTERMASS LIQUID FOR A SHOULDER LAUNCHED MUNITION PROPULSION SYSTEM

CROSS-REFERENCE TO RELATED APPLICATIONS

This application is the U.S. National Phase of PCT/US17/19749 filed on Feb. 27, 2017, which claims the benefit of U.S. Provisional Application No. 62/301,269, filed on Feb. 29, 2016, which are incorporated herein by reference.

FIELD OF THE INVENTION

The present invention relates to a countermass liquid, more particularly to a low-corrosion, high density, dispersible countermass liquid for a shoulder launched munition propulsion system, which utilizes the Davis Gun principle for accelerating a projectile in one direction and the countermass liquid in the opposing direction to minimize recoil, visual signature, and acoustic signature of the weapon.

BACKGROUND OF THE INVENTION

In the context of shoulder-fired weapons to be fired from an enclosure (FFE), the existing art uses a countermass fluid utilizing a Davis gun concept to balance physical and acoustic forces presenting hazards to the warfighter. The fluid itself is known to be a brine solution of aqueous calcium chloride. However, this approach is deficient because the countermass fluid comprises corrosive salts, which may become crystallized to some degree at extremely low temperatures.

Two principles can be used to launch projectiles from shoulder-fired weapons, or SFW: rocket propulsion, which can be safely used in outdoor combat, and the Davis gun concept, where gun-like propulsion recoil is counterbalanced. For combat involving firing the SFW from enclosed spaces, also referred to herein as FFE, rocket motors are undesirable due to increased fire hazard, pressure and noise in the enclosed space, at levels potentially harmful to the shooter. An SFW based on the Davis gun overcomes these issues.

In simplest form, the recoil from the Davis gun launch force needed to send the projectile down range is balanced against an opposite reaction force moving a countermass in the opposite direction. A number of different countermasses, also known as reaction masses, have been developed to reduce recoil, pressure and heat-signature, including liquids, metal and other powders, gels, plastic flakes, fiberglass, oil, sand, paper slips and jelly like-substances. However, many of these countermasses are not designed to be launched from enclosed spaces. Mixtures of solids and fluids may present viscosity, settling and dispersion problems. Countermass fluids tend to have a low density, which require large volumes for effectiveness, and are vulnerable to freezing at a wide temperature range.

U.S. Pat. No. 3,800,656 reports a launching device for a projectile with a high density flow medium held in the rear of the barrel interior by a removable element or burst membrane.

U.S. Pat. No. 6,543,329 reports a dispersible, nested ring-based countermass assembly, which is allegedly easily made chemically inert and non-toxic. Although the details of the countermass assembly are not explicitly disclosed, the materials are reported to be insensitive to changing and/or extreme temperatures.

U.S. Pat. No. 7,823,497 reports a countermass comprising an inner container made of a non-rigid material and an outer container designed with damping characteristics sealing the inner container. In the inner container is a countermass liquid with a high specific gravity such as fire extinguishing liquids, and a liquid binder having characteristics of Oasis type or other sponge like materials.

U.S. Pat. No. 4,554,860 reports a pressure damper for a recoilless weapon to reduce the pressure in the area around and immediately to the rear of the muzzle of the barrel. A container with liquid is placed in the barrel close to its muzzle or in a forward extended portion of the barrel and arranged to be burst when the weapon is fired so that the liquid is suddenly released and mixed with the powder gases. The celluloid container walls, which can be burst apart by the gases from the powder, is filled with a countermass fluid in the form of a salt solution, preferably containing calcium chloride.

U.S. Pat. No. 5,551,330 reports a dispersible countermass system for a recoilless weapon containing a charge of dispersible and inert matter disposed inside a case that is closed by a cover and by an end. The inert filler matter of the countermass is a liquid made up of water optionally including antifreeze such as calcium chloride. The addition of calcium chloride makes it possible to use the weapon at temperatures below 0° C. The relatively high density of the countermass liquid makes it possible to reduce the volume of the countermass.

Calcium chloride is used in de-icing aircraft. De-icing is accomplished using dry or liquid chemicals designed to lower the freezing point of water (various salts or brines, alcohols, glycols). Chemical de-icers include inorganic salts such as sodium chloride, magnesium chloride, calcium chloride, and potassium chloride; organic compounds such as calcium magnesium acetate, potassium acetate, potassium formate, sodium formate, calcium formate; urea, and agricultural by-products; and alcohols, diols and polyols such as methanol, ethylene glycol, propylene glycol, and glycerol.

Although using halide salts such as calcium chloride as the countermass liquid provides a high density ($>1$ gm/cm$^3$) salt solution, this fluid is corrosive to system materials, non-system materials and personnel. The corrosion problems associated with this fluid force certain system design solutions, specifically the need to isolate the countermass liquid in a separate countermass liquid container. This design deficiency greatly limits the design space. One approach to forming a low-corrosion countermass liquid is to suspend an iron oxide powder in water and incorporating a gelling compound, such as hydroxypropyl cellulose (HPC). However, this fluid has an undesirable level of variation in viscosity as a function of temperature. In addition, with long-term storage, the iron oxide may settle with potentially negative effects on system performance.

U.S. Pat. No. 8,707,847 reports a pollution-free liquid balancing device comprising liquid balancing matter, including water, anti-corrosion additives, antifreeze agents and inorganic salts. The mass of the liquid balancing matter is 1 to about 1.5 times that of the launch matter. The anti-corrosion additives and the antifreeze agents are liquid or soluble substances that do not react chemically with the sealing bag. The inorganic salts are also soluble substances that do not react chemically with the sealing bag, and the solubility is stable in the case of temperature changes. The sealing bag is filled with the liquid balancing matter, and plastically sealed under high temperatures at both ends. The anti-corrosion additives are reportedly used to adjust the pH of the liquid balancing matter, the anti-freeze agents are used to reduce the freezing point of the liquid balancing matter, and the inorganic salts are used to increase the density of the liquid balancing matter.

SUMMARY OF THE INVENTION

The present invention is directed to a countermass liquid for a shoulder launched munition propulsion system. The countermass liquid may have the following physical properties: low corrosivity; high density; low dynamic viscosity; constant viscosity as a function of temperature within an order of magnitude; low freezing point; high boiling point; constituents do not separate or precipitate out of solution; and constituents do not react with or thermally decompose due to propellant combustion within the shoulder launched munition propulsion system.

In one embodiment the countermass liquid may have: a density that is greater than 1 g/cm$^3$, a viscosity of less than 100 centipoise (cP) (as measured by ASTM D7483 test method); a constant viscosity as a function of temperature within an order of magnitude (i.e., at −20° F., the viscosity of the countermass liquid is no more than 70 cP., and at 130° F., the viscosity of the countermass liquid is no less than 20 cP); a freezing point less than −60° F.; a boiling point greater than 200° F.; and the constituents of the countermass liquid do not separate or precipitate out of solution (i.e., create a vertical density gradient).

The shoulder launched munition propulsion system may comprise a pressure vessel, wherein the pressure vessel houses: a projectile, disposed at the muzzle end of the weapon; a countermass liquid, disposed at the breach end of the weapon; a propellant charge, disposed between the projectile and the countermass liquid; a rupture disk, disposed at the forward end of the countermass liquid; and an aft seal disposed at the aft end of the weapon.

The countermass liquid may be released with the propellant gases that exit rearwardly from the weapon when the projectile is projected forward.

The countermass liquid may be composed of an organic salt solution. The organic salt solution may be selected from the group consisting of at least one or more of cesium formate and potassium formate.

In another embodiment, the countermass liquid may be an organic salt solution that is selected from the group consisting of at least one or more of cesium formate, potassium formate, cesium acetate, and potassium acetate. In this particular embodiment, the acetate may be used as buffering agent to control the pH for corrosion control.

In another embodiment, the countermass liquid may be an organic salt solution that is selected from the group composing of formate salts and acetate salts. In one particular embodiment, the countermass liquid may be selected from the group of cesium formate, potassium formate, cesium acetate, and potassium acetate. In this particular embodiment, the sodium may be used as a cation for the solution.

In another embodiment, the countermass liquid may be an organic salt solution that is selected from the group consisting of at least one or more of cesium formate, potassium formate, sodium formate, cesium acetate, and potassium acetate. In this particular embodiment, the acetate may be used as a buffering agent to control the pH for corrosion control.

The countermass liquid may have a density in the range of 1.0 to 2.4 g/cm$^3$ and is stable over a temperature range of −90° F. to +200° F.

The countermass liquid may be an aqueous true solution of cesium formate and potassium formate engineered to have the lowest true crystallization temperature. A true solution as used herein means a homogeneous solution composed of only one phase. A true crystallization temperature (TCT) as used herein means a temperature which a solid phase beings to form. A countermass liquid that has a low true crystallization is important at low temperatures where the phenomenon of supercooling can suppress nucleation, but if a seed crystal is introduced, crystallization can readily occur. The countermass liquid described herein has an adequately low true crystallization temperature to avoid crystallization at low temperatures when a seed crystal is introduced.

A countermass liquid that has low corrosivity allows the countermass liquid to be in direct contact with the housing components of the shoulder launched munition propulsion system, and does not require the propulsion system to include special coatings and/or additional components to house the countermass liquid to ensure that the countermass liquid does not damage the components of the system. Moreover, a countermass liquid having a low corrosivity reduces the potential for corrosion of non-system items that maybe in the vicinity of the system during functioning (i.e., minimize damage when the countermass liquid exits rearwardly from the munition propulsion system).

A countermass liquid with a high density ensures that the shoulder launched munition propulsion system efficiently utilizes the volume available for the countermass liquid. A countermass liquid with a low density would require more volume within the shoulder launched munition propulsion system, which adds costs and weight.

Low viscosity of the countermass liquid is critical as this is one of the primary contributors to load on the system during firing. The countermass liquid remains constant (within an order of magnitude) over a range of temperatures. In particular, at −20° F., the viscosity of the countermass liquid is no more than 70 cP., and at 130° F., the viscosity of the countermass liquid is no less than 20 cP.

Moreover, a countermass liquid with a high viscosity means that the shoulder launched munition propulsion system would be heavier than the system could be if the countermass liquid with low viscosity was used. The countermass liquid as described herein provides additional benefits by dampening hazards related to fire and air pressure transients. For packaging efficiency, high-density fluids are advantageous.

A countermass liquid that has a viscosity that is constant as a function of temperature allows the shoulder launched munition propulsion system to function across a broad temperature range. In particular, the recoil and load that occurs during the functioning of the shoulder launched munition propulsion system can change dramatically if the countermass liquid viscosity changes with temperature. The countermass of the invention can suitably be used in the countermass propulsion system described in the co-pending original U.S. patent application entitled "Countermass Propulsion System" (filed the same day as the instant application), which claims priority from Provisional Application No. 62/301,278 of the same title, the disclosures of which are incorporated herein in their respective entireties.

The above mentioned physical properties of the countermass liquid are stable across a wide temperature range for use within a weapon system, typically −60° F. to 160° F. Additionally, during the potential lifetime of the shoulder launched munition propulsion system (i.e., greater than 15 years), the countermass fluid has the following characteristics: does not separate over the potential lifetime of the system; the chemical stability remains constant; and the constituents within the countermass liquid do not react with or thermally decompose due to propellant combustion.

Additionally, the constituents of the countermass liquid do not create toxic bi-products during weapon system functioning (i.e., propellant combustion). A countermass liquid with a density of 1.75 g/cm$^3$ forms a eutectic which forms a condition such that the freezing point is the lowest with this specific ratio of cesium formate and potassium formate.

Within the scope of another embodiment, the countermass liquid may include, in relation to the total weight of the countermass liquid:

≥20 wt.-% though ≤40 wt. %, for example, ≥25 wt.-% though ≤35 wt. % potassium formate, where the potassium formate is 75% potassium formate and 25% water, and/or ≥31 wt.-% though ≤51 wt. %, for example, ≥36 wt.-% though ≤46 wt. % cesium formate, where the cesium formate solution is 80% cesium formate and 20% water, and/or ≥17 wt.-% though ≤37 wt. %, for example ≥22 wt.-% though ≤32 wt. % water.

Preferably, the sum of the weight-percent values may be 30.73% wt. potassium formate; 41.31% wt. cesium formate; and 27.96% wt. water.

The sum of the weight-percent values of potassium formate, cesium formate, and water results, in particular, in a total of 100 wt. %, in relation to the total weight of the countermass liquid.

Another object of the present invention is a method for manufacturing a countermass liquid for a shoulder launched munition system; in particular, an organic salt solution including the steps of:

A first step of blending potassium formate with cesium formate. Where the potassium formate solution is 75% potassium formate and 25% water, and the cesium formate solution is 80% cesium formate and 20% water. In one preferred embodiment, potassium formate having a density in the range of 1.0 g/cm$^3$ to 2.0 g/cm$^3$, preferably in the range of 1.5 g/cm$^3$ to 1.6 g/cm$^3$, more preferably having a density of 1.57 g/cm$^3$ is blended with cesium formate solution having a density in the range of 1.5 g/cm$^3$ to 2.5 g/cm$^3$, preferably in the range of 2.0 g/cm$^3$ to 2.30 g/cm$^3$, more preferably having a density of 2.20 g/cm$^3$. The blending of the potassium formate and cesium formate yields a potassium cesium formate blend. Preferably, the potassium cesium formate blend has a density in the range of 1.80 g/cm$^3$ to 2.0 g/cm$^3$, preferably the potassium cesium formate blend has a density of 1.90 g/cm$^3$.

In another embodiment, the potassium cesium blend may be generated by blending 39.35% by weight of the potassium formate with 60.65% by weight of the cesium formate solution. Preferably, the potassium cesium formate blend has a density in the range of 1.80 g /cm$^3$ to 2.0 g/cm$^3$, preferably the potassium cesium formate blend has a density of 1.90 g/cm$^3$.

A second step of diluting the potassium cesium formate blend to a diluted potassium cesium formate solution having a density in the range of 1.65 g/cm$^3$ to 1.85 g/cm$^3$, preferably in the range of 1.70 g/cm$^3$ to 1.80 g/cm$^3$, more preferably the diluted potassium cesium formate solution may have a density of 1.75 g/cm$^3$.

In another embodiment, the potassium cesium formate blend is diluted to a diluted potassium cesium formate solution by blending 83.33% of the 1.9 g/cm$^3$ potassium cesium formate blend with 16.67% water.

In another embodiment, the countermass liquid can be made by combining the following: 24.59% potassium formate salt, 40.43% cesium formate salt, and 34.97% water, which yields a potassium cesium formate blend with a density of 1.75 g/cm$^3$.

The countermass liquid described herein may be a solution and not a suspension or emulsion; therefore, suspended dense solids or liquids will not settle over time, which is one disadvantage in metal oxide-based suspension countermass fluids.

The countermass liquid blends described herein can be manipulated to achieve a large range of densities and other desirable physical properties, including density, true crystallization temperature, viscosity, viscosity as a function of temperature, and pH.

It is well known in the oil well completion area that potassium and cesium formate brines have a low tendency to cause corrosion. An additional benefit of the countermass liquid described herein is its low toxicity to life or the environment. Therefore, when the countermass liquid is dispersed from the weapon, reduced amounts of toxic or corrosive material come to rest on nearby surfaces. This is important for the warfighter both on the battlefield and in training operations where weapons may be fired many times within the same enclosure and/or on the same range.

DETAILED DESCRIPTION OF THE INVENTION

Figure 1:
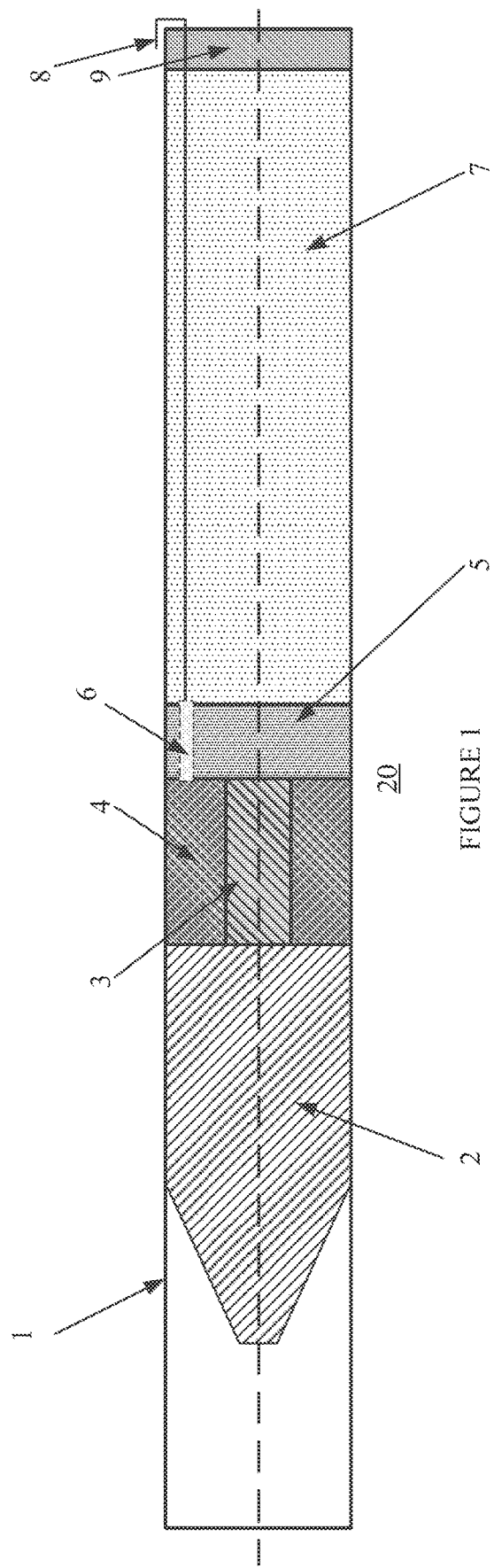
FIG. 1 illustrates a shoulder launched munition propulsion system.

FIG. 1 illustrates shoulder launched munition propulsion system 20 with countermass liquid 7. Shoulder launched munition propulsion system 20 may comprise pressure vessel 1. Pressure vessel 1 may house the following: projectile 2, retention means 3, solid propellant charge 4, rupture disk 5, ignition charge 6, countermass liquid 7, ignition line 8, and aft seal 9. Projectile 2 may be housed towards the muzzle end of pressure vessel 1 and aft seal 9 may be housed at the breach end of pressure vessel 1. Rupture disk 5 may be housed between projectile 2 and aft seal 9. Retention means 3 may be disposed between projectile 2 and rupture disk 5. Furthermore, retention means 3 may be attached to projectile 2 on one side and attached to rupture disk 5 on a second side. Solid propellant charge 4 may be disposed between projectile 2 and rupture disk 5 and may surround retention means 3.

Countermass liquid 7 may be disposed towards the breach end of pressure vessel 1 and may be disposed between rupture disk 5 and aft seal 9. Ignition line 8 may pass through aft seal 9, through countermass liquid 7, and may attach to ignition charge 6 on a first side. Alternatively, the ignition line 8 can be configured such that it does not go through the aft seal, but instead is positioned to proceed around the back of the pressure vessel 1 and between the pressure vessel 1 and the aft seal 9. Ignition charge 6 may be disposed through rupture disk 5 and have a first side facing countermass liquid 7 and a second side facing solid propellant charge 4.

The shoulder launched munition propulsion system 20 functions when a pyrotechnic event ignites ignition line 8. Ignition line 8 transfers the pyrotechnic charge through aft seal 9 and countermass liquid 7 to ignition charge 6. Ignition charge 6 transfers the pyrotechnic charge through rupture disk to solid propellant charge 4.

Figure 2:
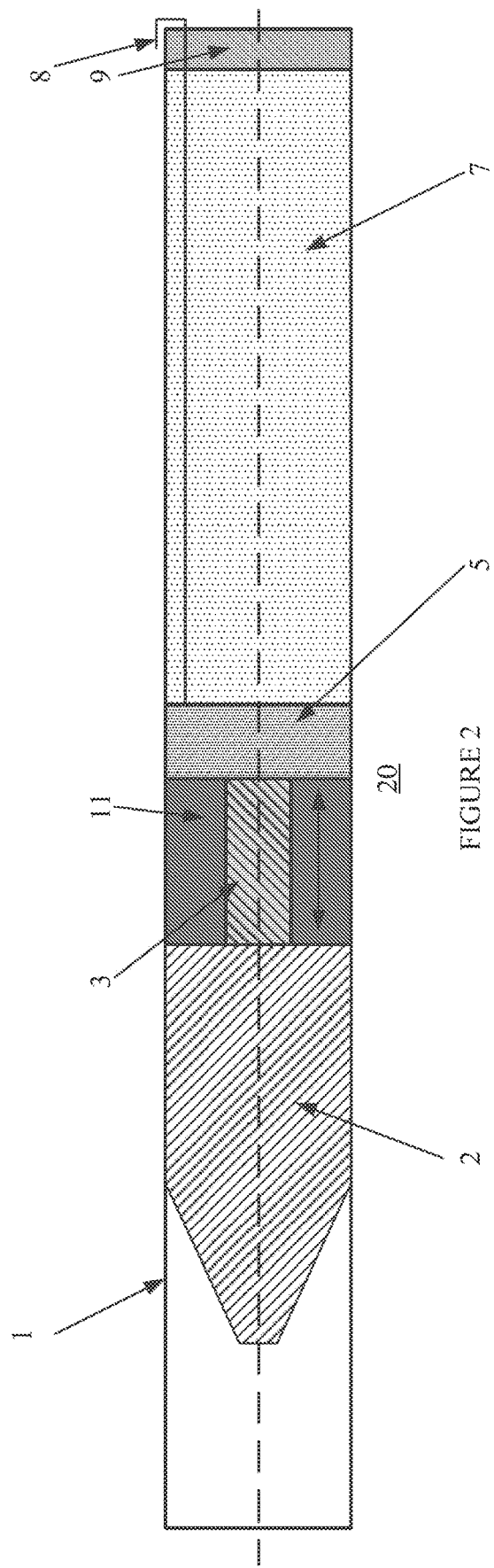
FIG. 2 illustrates a shoulder launched munition propulsion system during a first stage of operation.

Once the pyrotechnic charge reaches solid propellant 4, solid propellant charge is combusted into propellant gas 11, as shown in FIG. 2. As solid propellant charge 4 is transformed into propellant gas 11, the pressure inside pressure vessel 1 increases.

Figure 3:
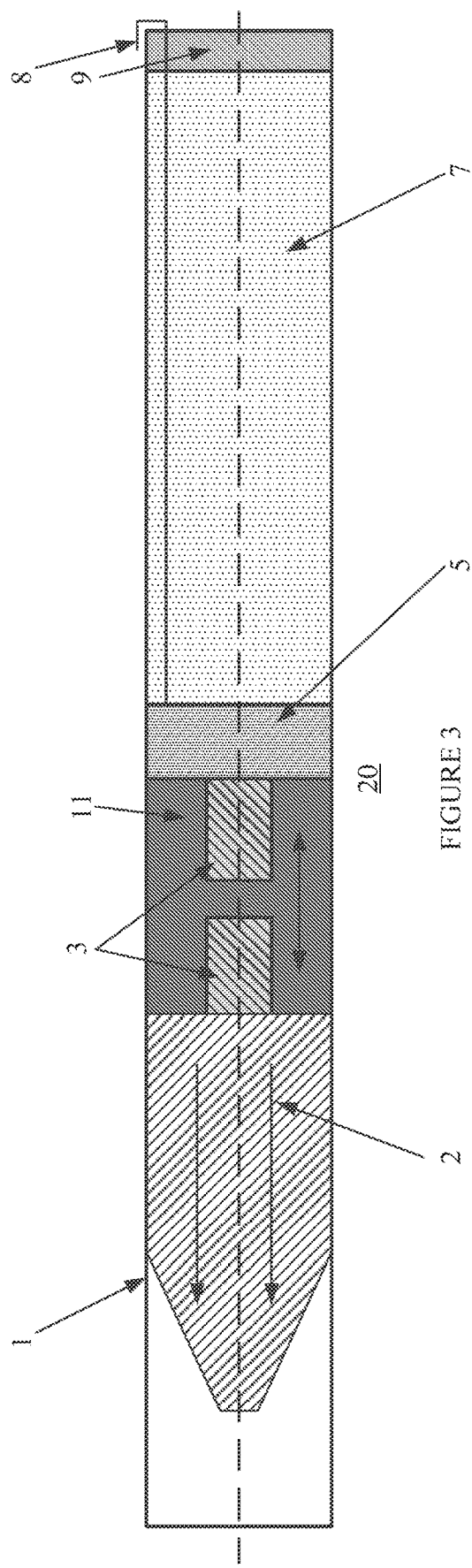
FIG. 3 illustrates a shoulder launched munition propulsion system during a second stage of operation.

FIG. 3 illustrates when the pressure inside pressure vessel 1 reaches a first predetermined value and retention means 3 releases projectile 2. Once retention means 3 releases projectile 2, propellant gas 11 exerts a force against projectile 2 which causes projectile 2 to move towards the muzzle end of pressure vessel 1.

Figure 4:
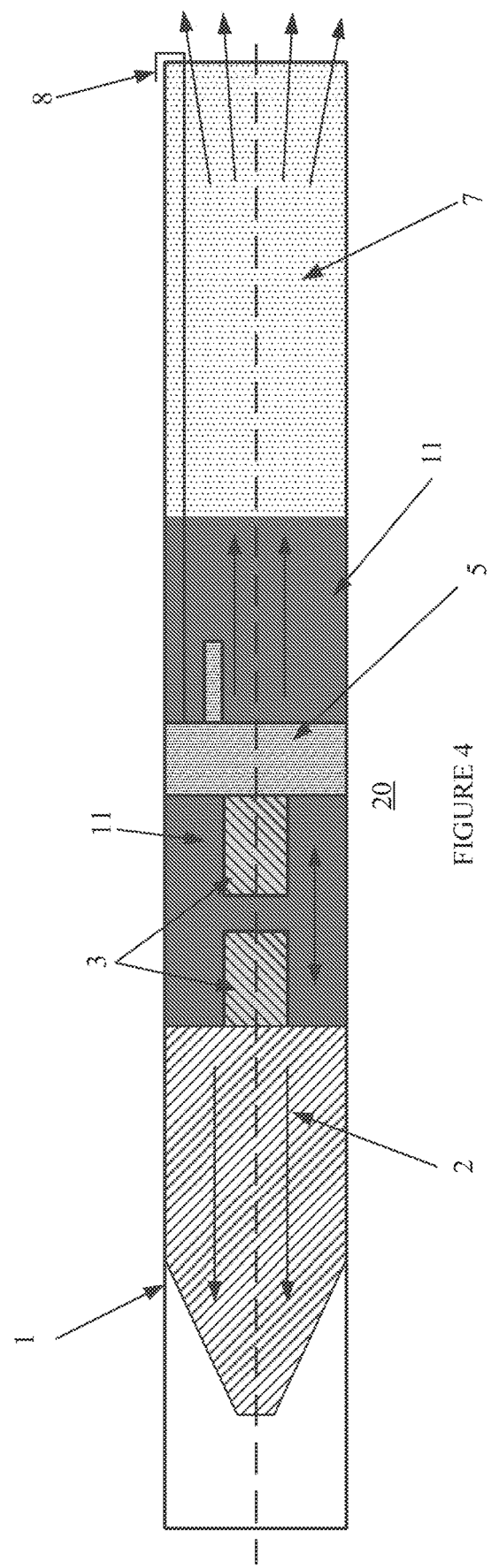
FIG. 4 illustrates a shoulder launched munition propulsion system during a third stage of operation.

As propellant gas 11 continues to expand, the pressure inside pressure vessel 1 continues to increase until the pressure reaches a second predetermined value. At this second predetermined value, rupture disk 5 opens and protrudes into countermass liquid 7, as shown in FIG. 4. The opening of rupture disk 5 allows propellant gas 11 to flow through rupture disk 5 towards countermass liquid 7. As propellant gas 11 flows through rupture disk 5 towards countermass liquid 7, propellant gas 11 exerts a force against countermass liquid 7, which causes countermass liquid to flow towards the breach end of pressure vessel 1. The force exerted against countermass liquid 7 by propellant gas 11 causes countermass liquid 7 to dislodge aft seal 9 [no longer depicted in FIG. 4 since it has ruptured] from pressure vessel 1 and exit pressure vessel 1 through the breach end of the pressure vessel.

Additionally, in FIG. 4, propellant gas continues to expand and increase the pressure inside pressure vessel 1. The increasing pressure in pressure vessel 1 continues to exert a force against projectile 2 in the direction of the muzzle end of pressure vessel 1, and projectile 2 continues to move towards the muzzle end of pressure vessel 1.

Figure 5:
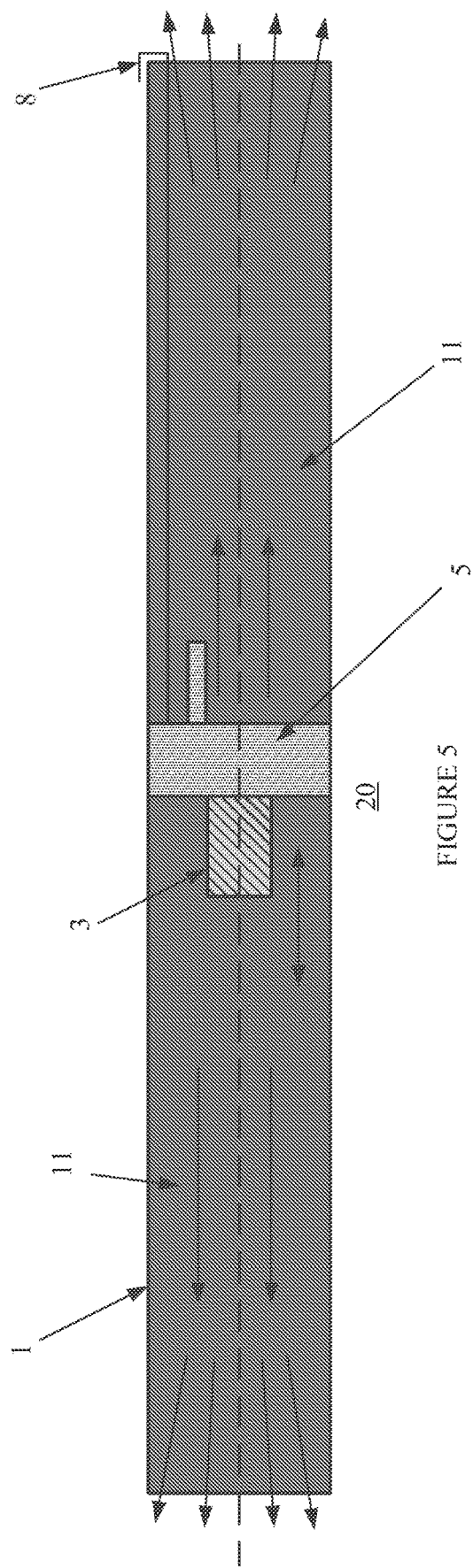
FIG. 5 illustrates a shoulder launched munition propulsion system during a fourth stage of operation.

FIG. 5 illustrates shoulder launched munition propulsion system 20 after projectile 2 has exited the muzzle end of pressure vessel 1 and after countermass liquid 7 has been completely ejected through the breach end of pressure vessel 1. When this occurs, propellant gas 11 exits through the muzzle and breach end of pressure vessel 1.

Countermass liquid 7 may have the following physical properties: low corrosivity; high density (i.e., greater than 1 grams/cubic centimeter); low viscosity (i.e., less than 100 centipoise); constant viscosity as a function of temperature, within an order of magnitude; low freezing point (i.e., less than −60° F.); high boiling point (i.e., greater than 200° F.); constituents do not separate or precipitated out of solution (i.e., do not create a vertical density gradient); and constituents do not react with or thermally decompose due to propellant combustion within the shoulder launched munition propulsion system.

Countermass liquid 7 may be an organic salt solution, selected from the group consisting of one or more of sodium formate, cesium formate, and potassium formate aqueous solutions.

EXAMPLES

Testing

Extensive testing was conducted to verify that the countermass liquid described herein did not degrade materials and/or components of the shoulder launched munition propulsion system that are in intimate contact with the fluid over the 10 year storage life of the system.

With respect to the extensive testing performed on the Cesium/Potassium Formate countermass fluid, such extensive testing was performed to evaluate the fluid properties for and within a weapon system. This was accomplished by evaluating the basic fluid properties by themselves, testing the fluid within the weapon system by utilizing hundreds of material coupons, and as a complete system by verifying the performance of the fluid in a total of 184 test firings. The 184 test firings were evaluated in accordance with MIL-STD-1474 "Design Criteria Standard Noise Limits" and ITOP-5-2-517 "Fire from Enclosure Testing," which are publically available, readily understood by those of ordinary skill in the art, and incorporated herein in their respective entireties by way of this reference. Regarding MIL-STD-1474, the inventors evaluated performance against both revision D and revision E of that standard. The inventors used raw sound data in their tests and, as a person of ordinary skill in the art would appreciate from reading both of these revisions D and E of the MIL-STD-1474, the calculation methods of both of these revisions are applicable to the tests.

The first series of testing was performed on the fluid to evaluate the basic fluid properties. Samples were taken to sub-freezing temperatures and evaluated for viscosity, crystallization temperature, and density. The second test series evaluated the effect of the fluid on commonly used materials that are likely to be found in system applications and looked for any degradation in structural properties of metallic and non-metallic materials while being exposed to the countermass fluid across a range of thermal environments. To evaluate these characteristics, several test samples types were utilized. Double lap shear coupons were prepared to evaluate non-metallics with adhesives. Cylindrical tensile specimens were manufactured for metallic samples, and composite tube sections were manufactured to evaluate effects on high performance composite tube pressure vessels. The tensile strength and overlap shear samples were sealed inside steel test vessels equipped with pressure sensors to monitor the pressure within the vessel. Composite tube sections were also prepared to contain the countermass fluid and represent storage. Data collected included pre and post test sample weights, ultrasonic images, photographs, mechanical load and elongation, pressure over time, and burst pressures.

Control samples were segregated, then the remainder of the samples were placed through the Joint Ordnance Test Procedure (JOTP)-010 thermal test profile, with a fraction of the samples being removed from the thermal exposure at three specified intervals throughout the test to evaluate trends based upon different environments. JOTP-010 is a publically available test procedure that is readily understood by those of ordinary skill in the art, and it is incorporated herein in its entirety by way of this reference. The intervals evaluated were after low temperature storage, solar radiation, and the remainder completed all testing, including 28 day high temperature cycling. After evaluation and data collection, the fluid was re-evaluated after testing to examine the post-test viscosity, crystallization temperature, and density.

A third series of testing was performed to evaluate the potential for galvanic corrosion between selected materials and the fluid. 90 samples were assembled and evaluated at three different test temperatures. Nammo Talley measured the current that flows between the anode and the cathode using a Zero Resistance Ammeter (ZRA) throughout the test at specified intervals. In addition, the part mass and dimensional characteristics of the part were measured pre and post test to identify any evidence of material degradation or corrosion. The results of testing indicated that there were no galvanic corrosion concerns with the samples evaluated.

In addition to the fluid and material compatibility tests performed, Nammo Talley also conducted testing of the fluid within the weapon system to evaluate the system performance. More than 100 test articles were evaluated for the system's ability to survive the necessary environmental conditions. All tests were performed at a variety of firing temperatures from −25F. to +140F. and after exposure to storage temperatures ranging from −60F to +160F. Test firings were performed and a variety of data was collected including: forward, aft and bending loads, pressure, and velocity. Specific tests were performed to measure the sound performance when fired from a standard enclosure, and evaluate the recoil performance, both attributes that the fluid has an effect on. Testing concluded that the countermass fluid is able to meet the inventive objectives of the system.

All of these tests performed provided data substantiating the design of the invention and its advantageous results.

Metallic component materials of the shoulder launched munition propulsion system that were tested included: stainless steel, 17-4 PH 1150, 304L, and 316L; Inconel 600; titanium, grade 5; and aluminum 7075 T651 with BR-127 primer and with electoless nickel. Non-metallic component materials of the shoulder launched munition propulsion system that were tested included: 4000 Halar tubing; Surlyn tubing; linear low density polyethylene (LLDPE); ethylene propylene diene monomer (EPDM); and silicone. The following adhesives were tested: epoxy, DP460, epoxy, DP125, and epoxy EC2216. The bond line control was approximately 0.007" spacer microspheres, 2% by weight. The substrate was stainless steel, H900, and the surface was prepared with BR-6747 primer.

Testing was performed to determine if metallic and nonmetallic sample material of the shoulder launched munition propulsion system degrade after being submerged in the countermass liquid while exposed to thermal environments, i.e., −90° F. to 200° F. Extensive testing showed that the metallic and non-metallic tested samples did not show a decrease in ultimate strength at any test point throughout the thermal exposure.

Testing was performed to determine if the adhesives of the shoulder launched munition propulsion system degrade structurally after submerged in the countermass liquid while exposed to thermal environments, i.e., −90° F. to 200° F. Extensive testing showed that the adhesive samples did not show a decrease in adhesive strength at any test point throughout the thermal exposure.

Testing was performed to determine if the metallic and nonmetallic components of the shoulder launched munition propulsion system reacted with the countermass liquid resulting in gas evolution. Extensive testing showed that the counter mass liquid did not exhibit gas generation when subjected to operating pressures, i.e., the countermass fluid did not increase the pressure inside test vessels. Additionally, the testing showed that the metallic and non-metallic samples did not show a pressure increase at any test point throughout the thermal exposure. Post environmental inspection did not show any visual discoloration from corrosion.

Testing was performed to determine if the properties of the countermass liquid changed after exposure to thermal environments, i.e., −90° F. to 200° F. Extensive testing showed that the countermass liquid material properties did not show significant change in terms of viscosity, crystallization temperature, pH, density, and conductivity. Additionally, testing showed that the counter mass liquid has minimal viscosity variation as a function of temperature, and the true crystallization temperature of the countermass fluid does not occur at −94° F. (−70° C.), even with nucleation material added.

Additionally, storage life accelerated aging testing indicated that the physical properties of the countermass liquid do not change with time and that the countermass liquid will not crystalize even when exposed to temperatures well below the storage limit of −60° F. The countermass liquid was also stable to temperature cycling and homogeneous nucleation conditions at temperatures well below the storage limit, i.e., there was no clouding, precipitation or crystal nucleation or growth.

Testing was performed to determine if the pressure vessel burst capability degrades after exposure to the thermal environments, i.e., −90° F. to 200° F., while filled with the countermass liquid. Testing was conducted with the pressure vessel filled with the countermass liquid and exposed to the thermal environments, i.e., −90° F. to 200° F., and testing was conducted with the pressure vessel exposed to thermal environments, i.e., −90° F. to 200° F., only. Extensive testing showed that sampled pressure vessels did not show a reduction in burst strength when exposed to thermal environments as well as combined thermal and countermass liquid exposure.

The invention claimed is:

1. A countermass liquid comprising an organic salt solution of water, cesium formate solution and potassium formate solution, wherein said organic salt solution has a density that is in the range of 1.70 g/cm$^3$ to 1.80 g/cm$^3$, a viscosity of less than 100 centipoise, as measured by ASTM D7483 test method, a constant viscosity as a function of temperature within an order of magnitude, a freezing point less than −60° F., and a boiling point greater than 200° F., and wherein the percent by weight of cesium formate salt in the organic salt solution is greater than or equal to 24.8% and less than or equal to 40.8% as compared to the total weight of the organic salt solution.

2. A countermass liquid comprising an organic salt solution of water, one or more formate salts, and one or more acetate salts, wherein solution has a density that is greater than 1 g/cm$^3$, a viscosity of less than 100 centipoise, as measured by ASTM D7483 test method, a constant viscosity as a function of temperature within an order of magnitude, a freezing point less than −60° F., and a boiling point greater than 200° F.

3. The countermass liquid of claim 2, wherein said formate salts comprise one or more of cesium formate, sodium formate and potassium formate.

4. The countermass liquid of claim 2, wherein said acetate salts comprise one or more of cesium acetate and potassium acetate.

5. The countermass liquid of claim 4, wherein said solution has a density in the range of 1.0 to 2.4 g/cm$^3$ and is stable over a temperature range of −90° F. to +200° F.

6. The countermass liquid of claim 5, wherein at −20° F., the viscosity of said solution is no more than 70 cP and, at 130° F., the viscosity of said solution is no less than 20 cP.

7. The countermass liquid of claim 1, wherein said organic salt solution is an aqueous true solution of cesium formate and potassium formate.

8. The countermass liquid of claim 1, wherein said organic salt solution has a density of about 1.75 g/cm$^3$.

9. A countermass liquid comprising an organic salt solution of water, cesium formate solution and potassium formate solution, wherein said organic salt solution has a density that is greater than or equal to 1.65 g/cm$^3$, a viscosity of less than 100 centipoise, as measured by ASTM D7483 test method, and a constant viscosity as a function of temperature within an order of magnitude, a freezing point less than −60° F. and a boiling point greater than 200° F., wherein said organic salt solution comprises: (a) from greater than or equal to 20 to less than or equal to 40 weight percent of said potassium formate solution, wherein said potassium formate solution comprises 75% potassium formate salt and 25% water by weight; (b) from greater than or equal to 31 to less than or equal to 51 weight percent of said cesium formate solution, wherein said cesium formate solution comprises 80% cesium formate salt and 20% water by weight; and (c) from greater than or equal to 17 to less than or equal to 37 weight percent of water.

10. The countermass liquid of claim 9, wherein said organic salt solution further comprises sodium formate.

11. The countermass liquid of claim 3, wherein said organic salt solution has a density in the range of 1.65 to 2.4 g/cm$^3$ and is stable over a temperature range of −90° F. to +200° F.

12. The countermass liquid of claim 3, wherein at −20° F., the viscosity of said organic salt solution is no more than 70 cP and, at 130° F., the viscosity of said solution is no less than 20 cP.

13. The countermass liquid of claim 9, wherein said organic salt solution comprises: (a) from greater than or equal to 25 to less than or equal to 35 weight percent of said potassium formate solution, wherein said potassium formate solution comprises 75% potassium formate salt and 25% water by weight; (b) from greater than or equal to 36 to less than or equal to 46 weight percent of said cesium formate solution, wherein said cesium formate solution comprises 80% cesium formate salt and 20% water by weight; and (c) from greater than or equal to 22 to less than or equal to 32 weight percent of water.

14. The countermass liquid of claim 12, wherein said organic salt solution comprises: about 16.67 weight percent of water and 83.33 weight percent of an organic salt solution of (a) about 39.35 weight percent of said potassium formate solution, wherein said potassium formate solution comprises 75% potassium formate salt and 25% water by weight;

and (b) about 60.65 weight percent of said cesium formate solution, wherein said cesium formate solution comprises 80% cesium formate salt and 20% water by weight.

15. The countermass liquid of claim 12, wherein said organic salt solution comprises: (a) about 24.59 weight percent potassium formate salt; (b) about 40.43 weight percent cesium formate salt; and (c) about 34.97 weight percent water.

* * * * *